(12) United States Patent
Park et al.

(10) Patent No.: US 11,076,833 B2
(45) Date of Patent: Aug. 3, 2021

(54) ULTRASOUND IMAGING APPARATUS AND METHOD FOR DISPLAYING ULTRASOUND IMAGE

(71) Applicant: Samsung Medison Co., Ltd., Gangwon-do (KR)

(72) Inventors: Seok-lai Park, Seongnam-si (KR); Rae-Eun Kim, Seongnam-si (KR); Sun-joong Lee, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 0 days.

(21) Appl. No.: 16/509,202

(22) Filed: Jul. 11, 2019

(65) Prior Publication Data

US 2020/0029940 A1 Jan. 30, 2020

Related U.S. Application Data

(60) Provisional application No. 62/702,578, filed on Jul. 24, 2018.

(30) Foreign Application Priority Data

Nov. 15, 2018 (KR) .................. 10-2018-0141135

(51) Int. Cl.
*A61B 8/08* (2006.01)
*G09G 3/20* (2006.01)

(52) U.S. Cl.
CPC ......... *A61B 8/5246* (2013.01); *G09G 3/2092* (2013.01); *G09G 2310/0205* (2013.01); *G09G 2310/0213* (2013.01); *G09G 2380/08* (2013.01)

(58) Field of Classification Search
CPC .................................................. A61B 8/5246
(Continued)

(56) References Cited

U.S. PATENT DOCUMENTS 6,097,357 A * 8/2000 Shinoda ............... G09G 3/2022
313/485
6,224,552 B1 5/2001 Jago et al.
(Continued)

FOREIGN PATENT DOCUMENTS

| JP | 3863791 B2 | 10/2006 |
| KR | 10-1175497 A | 8/2012 |
| KR | 10-1555259 B1 | 9/2015 |

*Primary Examiner* — Javid A Amini
(74) *Attorney, Agent, or Firm* — Morgan, Lewis & Bockius LLP

(57) ABSTRACT

Provided are an ultrasound imaging apparatus and method for displaying an ultrasound image. The ultrasound imaging apparatus includes: a display; and a processor configured to set, from among a plurality of scan lines, a plurality of scan line groups respectively corresponding to a plurality of subframes constituting a first frame, control the display to display the first frame, set, from among the plurality of scan lines, a plurality of scan line groups respectively corresponding to a plurality of subframes constituting a second frame, and control the display to display the second frame subsequently to the first frame. The processor may set the plurality of scan line groups such that a position of a boundary line between adjacent ones of the plurality of subframes in the first frame does not overlap a position of a boundary line between adjacent ones of the plurality of subframes in the second frame.

20 Claims, 10 Drawing Sheets

(58) Field of Classification Search
USPC .......................................................... 345/629
See application file for complete search history.

(56) References Cited

U.S. PATENT DOCUMENTS

| | | | |
|---|---|---|---|
| 6,390,981 | B1 | 5/2002 | Jago |
| 6,537,217 | B1 | 3/2003 | Bjaerum et al. |
| 8,968,199 | B2 | 3/2015 | Kim |
| 2002/0190930 | A1* | 12/2002 | Shiizaki ................ G09G 3/299 345/63 |
| 2005/0116904 | A1* | 6/2005 | Adachi ................ G09G 3/3216 345/76 |
| 2006/0017667 | A1* | 1/2006 | Seki .................... G09G 3/3233 345/76 |
| 2006/0044231 | A1* | 3/2006 | Seki .................... G09G 3/2055 345/76 |
| 2007/0106155 | A1* | 5/2007 | Goodnow ............... A61B 8/12 600/437 |
| 2014/0039317 | A1 | 2/2014 | Sato |
| 2015/0150540 | A1* | 6/2015 | Cai .................... A61B 8/4461 600/445 |
| 2016/0089116 | A1 | 3/2016 | Duncan et al. |
| 2017/0020487 | A1 | 1/2017 | Chang et al. |

* cited by examiner

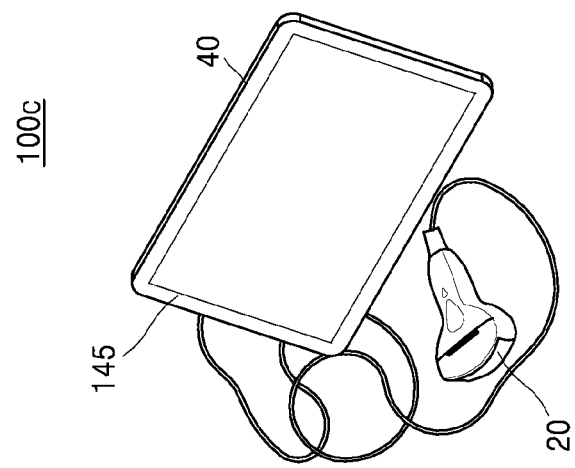
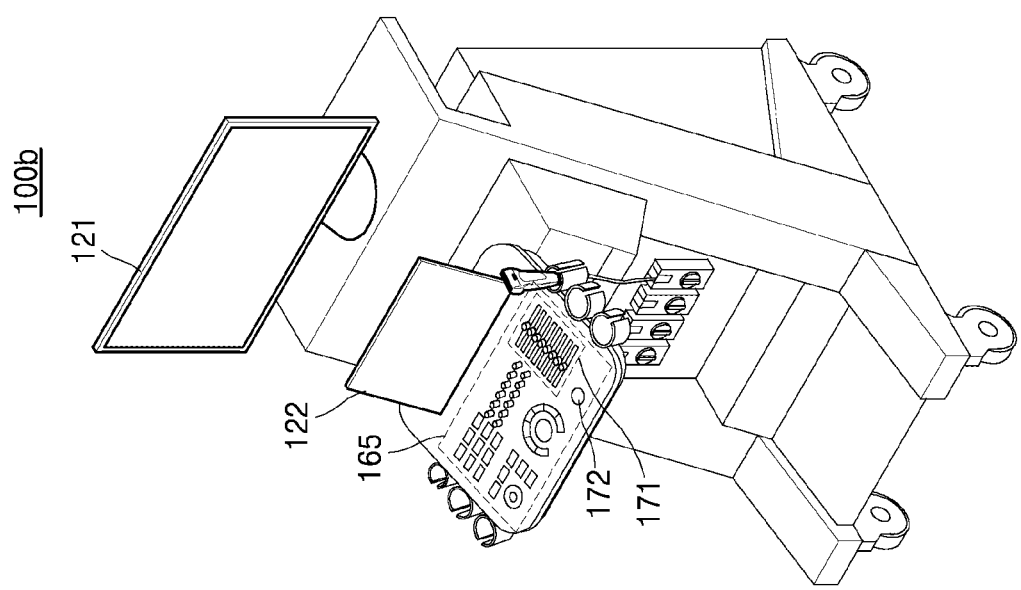
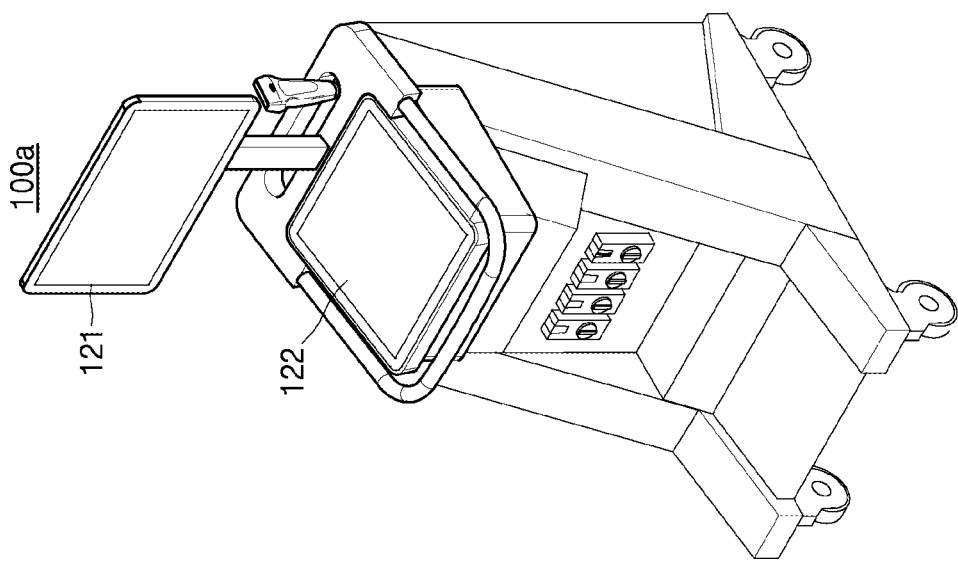

ULTRASOUND IMAGING APPARATUS AND METHOD FOR DISPLAYING ULTRASOUND IMAGE

CROSS-REFERENCE TO RELATED APPLICATION(S)

This application claims the benefit of U.S. Provisional Application No. 62/702,578, filed on Jul. 24, 2018, in the US Patent Office and Korean Patent Application No. 10-2018-0141135, filed on Nov. 15, 2018, in the Korean Intellectual Property Office, the disclosures of which are incorporated herein in their entireties by reference.

BACKGROUND

1. Field

The disclosure relates to ultrasound imaging apparatuses and methods, and more particularly, to ultrasound imaging apparatuses and methods for displaying an image by using an ultrasound image composed of a plurality of subframes.

2. Description of Related Art

Ultrasound diagnosis apparatuses transmit ultrasound signals generated by transducers of a probe to an object and receive information of signals reflected from the object, thereby obtaining at least one image of an internal part (e.g., soft tissues or blood flow) of the object. In particular, ultrasound diagnosis apparatuses are used for medical purposes including observing an internal area of an object, detecting foreign substances, and assessing injuries. Such ultrasound diagnosis apparatuses exhibit high stability, display images in real-time, and are safe due to lack of radiation exposure, compared to diagnostic X-ray apparatuses. Therefore, ultrasound diagnosis apparatuses have been widely used together with other types of imaging diagnosis apparatuses including a computed tomography (CT) apparatus and a magnetic resonance imaging (MRI) apparatus.

SUMMARY

Provided are methods and apparatuses for providing an ultrasound image more smoothly, and in particular, methods and apparatus for more smoothly providing an ultrasound image including a frame composed of a plurality of subframes.

Additional aspects will be set forth in part in the description which follows and, in part, will be apparent from the description, or may be learned by practice of the presented embodiments.

In accordance with an aspect of the disclosure, an ultrasound imaging apparatus includes: a display; and a processor configured to set, from among a plurality of scan lines, a plurality of scan line groups respectively corresponding to a plurality of subframes constituting a first frame, control the display to display the first frame, set, from among the plurality of scan lines, a plurality of scan line groups respectively corresponding to a plurality of subframes constituting a second frame, and control the display to display the second frame subsequently to the first frame. The processor may set the plurality of scan line groups such that a position of a boundary line between adjacent ones of the plurality of subframes in the first frame does not overlap a position of a boundary line between adjacent ones of the plurality of subframes in the second frame.

BRIEF DESCRIPTION OF THE DRAWINGS

These and/or other aspects will become apparent and more readily appreciated from the following description of the embodiments, taken in conjunction with the accompanying drawings in which:

FIGS. 2A, 2B, and 2C are diagrams respectively illustrating an ultrasound diagnosis apparatus according to an exemplary embodiment;

DETAILED DESCRIPTION

Figure 1:
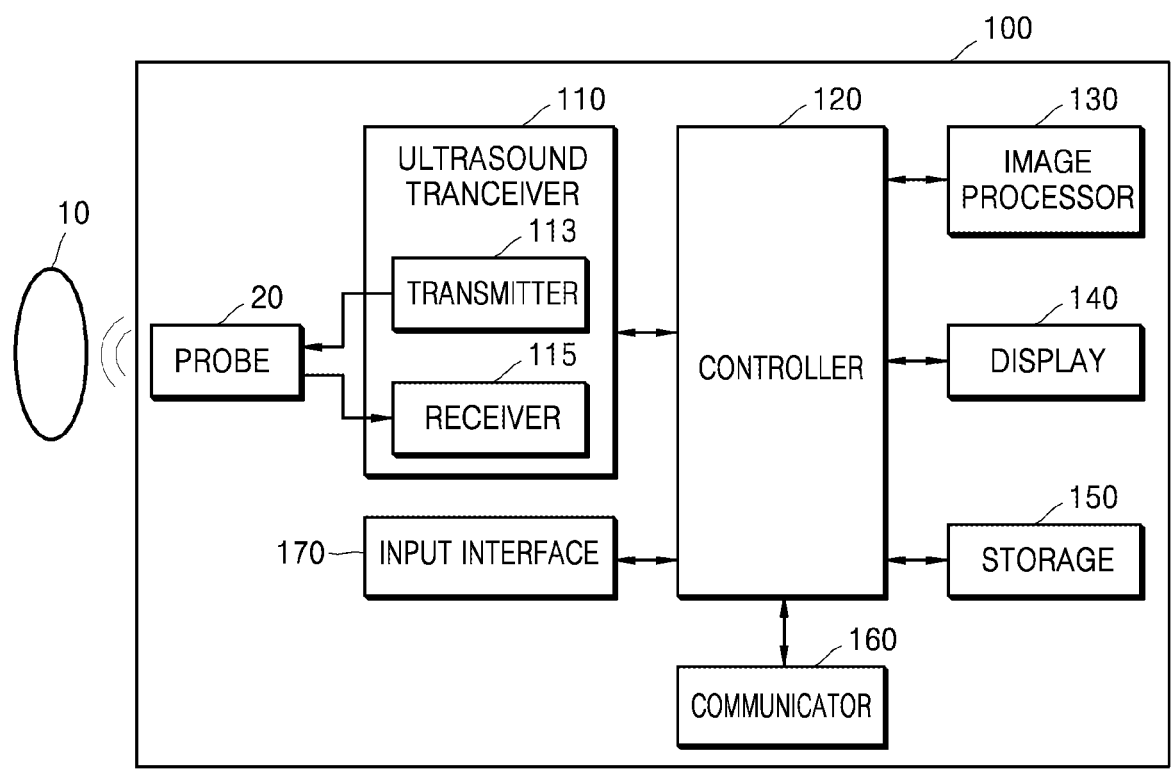
FIG. 1 is a block diagram illustrating an ultrasound diagnosis apparatus according to an exemplary embodiment.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

Like reference numerals refer to like elements throughout. The present specification does not describe all components in the embodiments, and common knowledge in the art or the same descriptions of the embodiments will be omitted below. The term "part" or "portion" used herein may be implemented using hardware or software, and according to embodiments, a plurality of "parts" or "portions" may be formed as a single unit or element, or one "part" or "portion" may include a plurality of units or elements. Expressions such as "at least one of," when preceding a list of elements, modify the entire list of elements and do not modify the individual elements of the list. Hereinafter, the operating principles and embodiments of the disclosure will be described in detail with reference to the accompanying drawings.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

FIGS. 2A, 2B, and 2C are diagrams illustrating ultrasound diagnosis apparatus according to an exemplary embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUI), thereby receiving user's inputs of data to control the ultrasound diagnosis apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100 may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100 may include a portable device. An example of the portable ultrasound diagnosis apparatus 100 may include, for example, smart phones including probes and applications, laptop computers, personal digital assistants (PDAs), or tablet PCs, but an exemplary embodiment is not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

Figure 3:
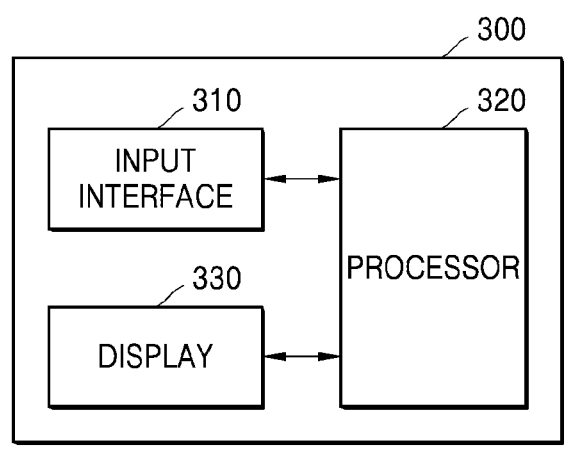
FIG. 3 is a block diagram of a configuration of an ultrasound imaging apparatus according to an embodiment.

FIG. 3 is a block diagram of a configuration of an ultrasound imaging apparatus 300 according to an embodiment.

Referring to FIG. 3, the ultrasound imaging apparatus 300 includes an input interface 310, a processor 320, and a display 330. The ultrasound imaging apparatus 300 may correspond to the ultrasound diagnosis apparatus 100 of FIG. 1. Furthermore, the ultrasound imaging apparatus 300 may be implemented in the same form as the ultrasound diagnosis apparatus 100A, 100B, or 100C described with reference to FIG. 2. In an embodiment, the input interface of FIG. 3 may include the input interface 170 described with reference to FIG. 1. Furthermore, the processor 320 may correspond to the controller 120 and the image processor 130 described with reference to FIG. 1. The processor 320 may include one or a plurality of processors. The display 330 may correspond to the display 140 described with reference to FIG. 1.

According to an embodiment, the ultrasound imaging apparatus 300 may include fewer components than those shown in FIG. 3 or may further include another component. For example, the ultrasound imaging apparatus 300 may not include the input interface 310 and receive a user input from a separate device.

According to an embodiment, the ultrasound imaging apparatus 300 may include a probe (not shown) configured to transmit ultrasound signals to an object and detect ultrasound echo signals. In an embodiment, the probe may transmit ultrasound signals to the object along a plurality of scan lines and receive ultrasound echo signals reflected from the object.

The processor 320 may acquire ultrasound data with respect to an object from ultrasound echo signals. According to an embodiment, the processor 320 may acquire brightness (B) mode image data with respect to a region of interest (ROI) from ultrasound echo signals. Alternatively, the processor 320 may acquire, based on ultrasound echo signals, ultrasound image data including at least one of spectral Doppler image data, color Doppler image data, elasticity image data, and motion (M) mode image data with respect to an ROI, but types of ultrasound image data that are to be acquired by the processor 320 are not limited thereto. The color Doppler image data may include at least one of blood flow Doppler image data and tissue Doppler image data.

In the present disclosure, an ROI may be a specific region of an object of which an ultrasound image is to be generated, such as a region of the object including a particular lesion. However, the ROI is not limited to the above-described example.

According to an embodiment, the processor 320 may generate an ultrasound image based on acquired ultrasound data in units of subframes. In detail, the processor 320 may generate a plurality of subframes that constitute a frame, each subframe representing a portion of an image of an ROI. Furthermore, a frame formed by the processor 320 may correspond to the entire image of an ROI displayed on the display 330 or a portion of the entire image. For example, the processor 320 may align subframes adjacent to one another to form a single frame.

According to an embodiment, the processor 320 may set, from among a plurality of scan lines, a plurality of scan line groups respectively corresponding to a plurality of subframes that form a first frame. In this case, each of the set scan line groups may include a plurality of scan lines for acquiring data corresponding to each subframe.

The processor 320 may transmit an ultrasound signal to a target position on a determined scan line group. The ultrasound imaging apparatus 300 may generate a subframe by using an ultrasound echo signal acquired in response to the transmitted ultrasound signal.

According to an embodiment, the plurality of subframes may each have the same size. In other words, each scan line group corresponding to a subframe may include the same number of scan lines.

According to an embodiment, the plurality of subframes may be acquired in an interleaved manner. For example, the processor 320 may discontinuously generate the plurality of subframes by allowing ultrasound signals to be discontinuously transmitted to the plurality of scan line groups.

The processor 320 may control the display 330 to display the first frame. In an embodiment, the processor 320 may control the display 330 to display the first frame on a subframe-by-subframe basis. For example, the processor 320 may control the display 330 such that a plurality of subframes constituting the first frame are sequentially accumulated in the order that they are generated and then displayed. In detail, when the first frame includes first through third subframes, the processor 320 may control the display 330 to first display the first subframe, then display the first and second subframes together when the second subframe is generated, and finally display the first through third subframes together when the third subframe is generated. Alternatively, the processor 320 may control the display 330 to simultaneously display the plurality of subframes forming the first frame.

According to an embodiment, the processor 320 may determine a plurality of subframes that constitute a second frame showing an ROI. In this case, the second frame may be displayed on the display 330 successively to the first frame. On the display 330, positions of the plurality of subframes forming the second frame may be different from positions of the subframes forming the first frame. In detail, the processor 320 may determine the plurality of subframes forming the second frame in such a manner that a position of a boundary line between adjacent ones of the subframes in the first frame does not overlap a position of a boundary line between adjacent ones of the subframes in the second frame.

According to an embodiment, the processor 320 may set the number of scan lines included in a scan line group corresponding to a subframe to a number other than a divisor of the number of all the scan lines. An operation of the processor 320 setting the number of scan lines and accordingly setting a subframe will be described in more detail below with reference to FIGS. 4 and 5.

According to an embodiment, the processor 320 may set a plurality of scan line groups such that a first scan line corresponding to a first subframe among the plurality of subframes in the second frame is located next to a last scan line corresponding to a last subframe among the plurality of subframes in the first frame.

According to an embodiment, the processor 320 may further include a memory for storing a predetermined subframe sequence. The processor 320 may set a plurality of scan line groups based on the subframe sequence stored in the memory. In this case, the subframe sequence may be information indicative of scan line groups that are to be selected to repeatedly generate subframes during acquisition of an ultrasound image.

The processor 320 may be formed as a hardware unit including a memory and a processor. The memory stores at least one of application data, an algorithm, and a program for performing calculations such that a position of a boundary line between adjacent ones of the subframes in the first frame does not overlap a position of a boundary line between adjacent ones of the subframes in the second frame. The processor processes the program, algorithm, or application data stored in the memory. For example, the processor 320 may consist of a processor including at least one of a central processing unit (CPU), a microprocessor, and a graphic processing unit (GPU). In this case, the memory and the processor may be formed as a single chip, but are not limited thereto.

Figure 4:
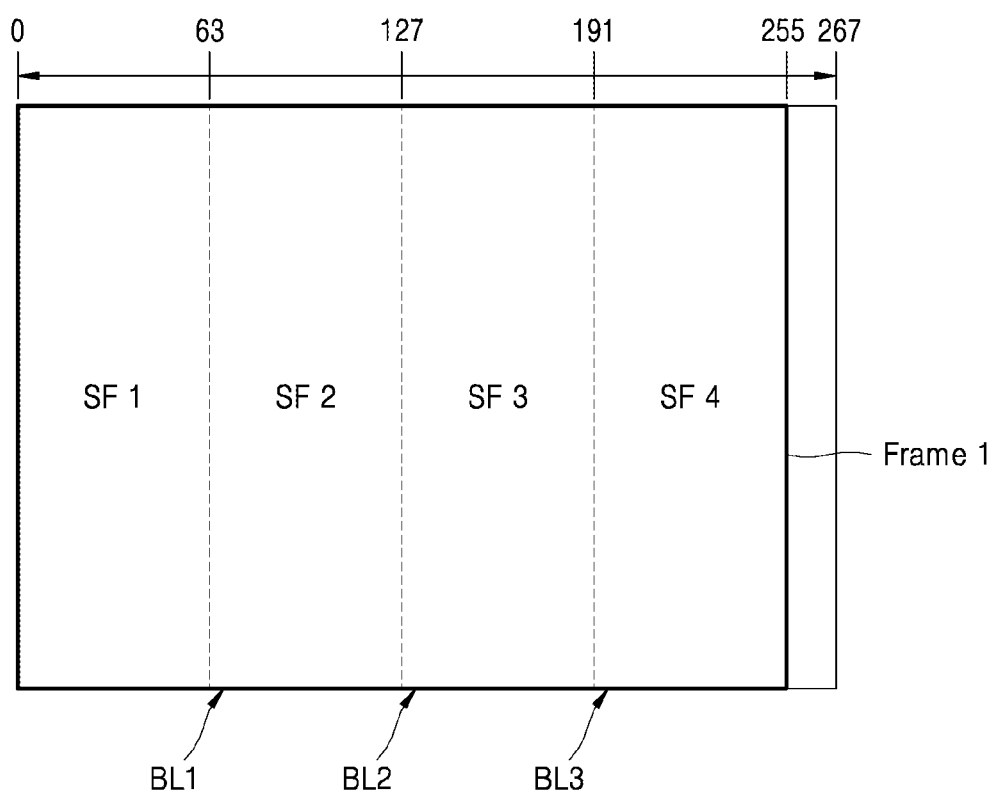
FIG. 4 illustrates a method whereby an ultrasound imaging apparatus generates a first frame, according to an embodiment.

FIG. 4 illustrates a method whereby an ultrasound imaging apparatus generates a first frame, according to an embodiment.

Referring to FIG. 4, a first frame Frame 1 may be a portion of the entire ultrasound image 400 of an ROI. However, this is merely an example, and the first frame Frame 1 may include all portions of the entire ultrasound image 400. In addition, although FIG. 4 shows that the first frame Frame 1 includes four subframes SF1 through SF4, this is merely an example, and it will be fully understood by those of ordinary skill in the art that the number of subframes contained in the first frame Frame 1 is not limited to 4.

FIG. 4 illustrates an example in which the entire ultrasound image 400 of the ROI is obtained in correspondence to a plurality of scan lines 0 through 267, i.e., 268 scan lines, and the first frame Frame 1 is acquired in correspondence to 256 scan lines 0 through 255. In this case, the ultrasound imaging apparatus may determine a plurality of subframes SF1 through SF4 forming the first frame Frame 1 and set, from among the plurality of scan lines 0 through 267, a plurality of scan line groups respectively corresponding to the determined subframes SF1 through SF4. For example, the ultrasound imaging apparatus may set a scan line group including scan lines 0 through 63 corresponding to a first subframe SF1, a scan line group including scan lines 64 through 127 corresponding to a second subframe SF2, a scan line group including scan lines 128 through 191 corresponding to a third subframe SF3, and a scan line group including scan lines 192 through 255 corresponding to a fourth subframe SF4. Although FIG. 4 shows scan lines in one scan line group as continuous scan lines, according to an embodiment, scan lines in a scan line group corresponding to a single subframe may be discontinuous scan lines. For example, one subframe may be acquired in correspondence to discontinuous scan lines 256 through 267 and 0 through 51.

The ultrasound imaging apparatus may generate the first frame Frame 1 by using the subframes SF1 through SF4 respectively acquired in correspondence to the scan line groups. For example, the ultrasound imaging apparatus may generate the first frame Frame 1 by arranging the subframes SF1 through SF4 adjacent to one another. In this case, boundary lines BL1 through BL3 may each exist between adjacent ones of the subframes SF1 through SF4 forming the first frame Frame 1.

Figure 5:
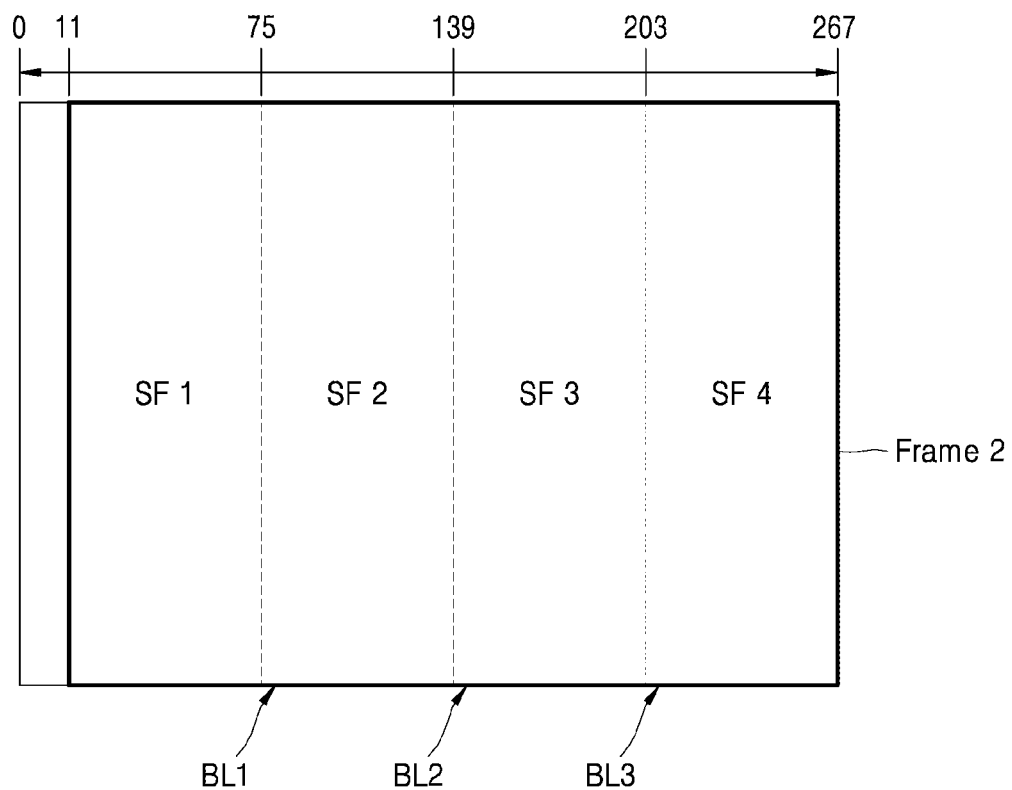
FIG. 5 illustrates a method whereby an ultrasound imaging apparatus generates a second frame, according to an embodiment.

FIG. 5 illustrates a method whereby an ultrasound imaging apparatus generates a second frame, according to an embodiment.

Referring to FIG. 5, a second frame Frame 2 may be a portion of the entire ultrasound image 500 of an ROI. However, this is merely an example, and the second frame Frame 2 may include all portions of the entire ultrasound image 500. In addition, although FIG. 5 shows that the second frame Frame 2 includes four subframes SF1 through SF4, it will be fully understood by those of ordinary skill in the art that the number of subframes contained in the second frame Frame 2 is not limited to 4.

FIG. 5 illustrates an example in which the entire ultrasound image 500 of the ROI is obtained in correspondence to a plurality of scan lines 0 through 267, i.e. 268 scan lines, and the second frame Frame 2 is acquired in correspondence to 256 scan lines 11 through 267. In this case, the ultrasound imaging apparatus may determine a plurality of subframes SF1 through SF4 forming the second frame Frame 2 such that a position of a boundary line between adjacent ones of subframes in a first frame displayed earlier than the second frame Frame 2 does not overlap a position of a boundary line between adjacent ones of the subframes SF1 through SF4 in the second frame Frame 2.

Furthermore, the ultrasound imaging apparatus set, from among the plurality of scan lines 0 through 267, a plurality of scan line groups respectively corresponding to the determined subframes SF1 through SF4. For example, the ultrasound imaging apparatus may set a scan line group including scan lines 11 through 74 corresponding to a first subframe SF1, a scan line group including scan lines 75 through 138 corresponding to a second subframe SF2, a scan line group including scan lines 139 through 202 corresponding to a third subframe SF3, and a scan line group including scan lines 203 through 267 corresponding to a fourth subframe SF4.

The ultrasound imaging apparatus may generate the second frame Frame 2 by using the subframes SF1 through SF4 respectively acquired in correspondence to the scan line groups. In this case, boundary lines BL1 through BL3 may each exist between adjacent ones of the subframes SF1 through SF4 forming the second frame Frame 2.

As described with reference to FIGS. 4 and 5, the ultrasound imaging apparatus may set a plurality of subframes and their corresponding scan line groups for first and second frames such that a position of a boundary line between adjacent ones of a plurality of subframes in the first frame does not overlap a position of a boundary line between adjacent ones of a plurality of subframes in the second frame. According to an embodiment, the ultrasound imaging apparatus is configured such that a boundary line between subframes in one frame does not overlap a boundary line between subframes in another frame displayed on a display successively to the one frame, thereby reducing seam artifacts occurring in an ultrasound image.

In the embodiments described with reference to FIGS. 4 and 5, positions of the first frame Frame 1 and the second frame Frame 2 are set to be different from each other, and sizes of the subframes SF1 through SF4 are set to be equal to each other. However, a method of setting a subframe is not limited to the embodiments. For example, the ultrasound imaging apparatus may vary the size of each subframe such that a position of a boundary line between a plurality of subframes in a first frame does not overlap a position of a boundary line between a plurality of subframes in a second frame.

Figure 6:
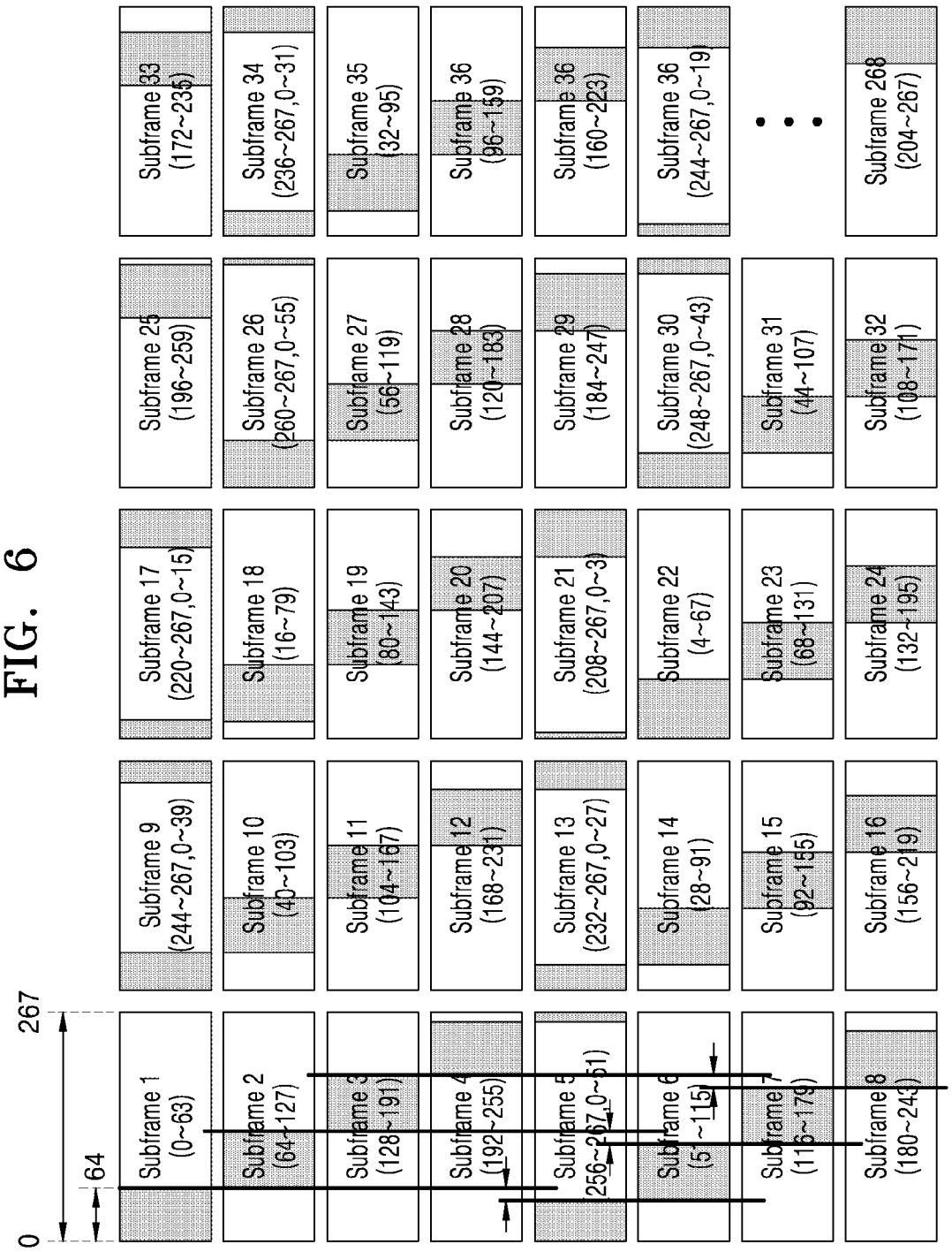
FIG. 6 illustrates a subframe sequence according to an embodiment.

FIG. 6 illustrates a subframe sequence according to an embodiment.

Referring to FIG. 6, an ultrasound imaging apparatus may select scan line groups by iteratively referring to a subframe sequence including 268 subframes. In an embodiment, the number of scan lines corresponding to each subframe is equally 64, and the subframe sequence may include 67 frames. However, this is merely an example, and it will be appreciated by those of ordinary skill in the art that the numbers of subframes and frames in the subframe sequence are not limited thereto.

Referring to FIG. 6, the ultrasound imaging apparatus may generate a first frame including first through fourth subframes. Furthermore, the ultrasound imaging apparatus may generate a second frame including fifth through eighth subframes.

In an embodiment, a first scan line in each subframe may be set to be located next to a last scan line in its preceding subframe. Furthermore, the ultrasound imaging apparatus may set a scan line group such that a first scan line 0 is selected again after a last scan line 267 is selected. For example, the ultrasound imaging apparatus may set a scan line group including scan lines 256 through 267 and 0 through 51 corresponding to a fifth subframe after setting a scan line group including scan lines 192 through 255 corresponding to a fourth subframe.

According to an embodiment, the ultrasound imaging apparatus may set the number of scan lines corresponding to each subframe to a number other than a divisor of the number of all scan lines. In other words, the ultrasound imaging apparatus may set positions of subframes in consecutive frames to be different from each other by making a total number of scan lines in one frame different from the number of all the scan lines.

Furthermore, in an embodiment, the ultrasound imaging apparatus may set the subframe sequence such that a last scan line in a scan line group corresponding to a 268-th subframe that is a last subframe in the subframe sequence ends with the last scan line 267 among all the scan lines. In this way, the ultrasound imaging apparatus may continuously acquire an ultrasound image corresponding to each subframe by repeatedly referring to the subframe sequence.

Figure 7:
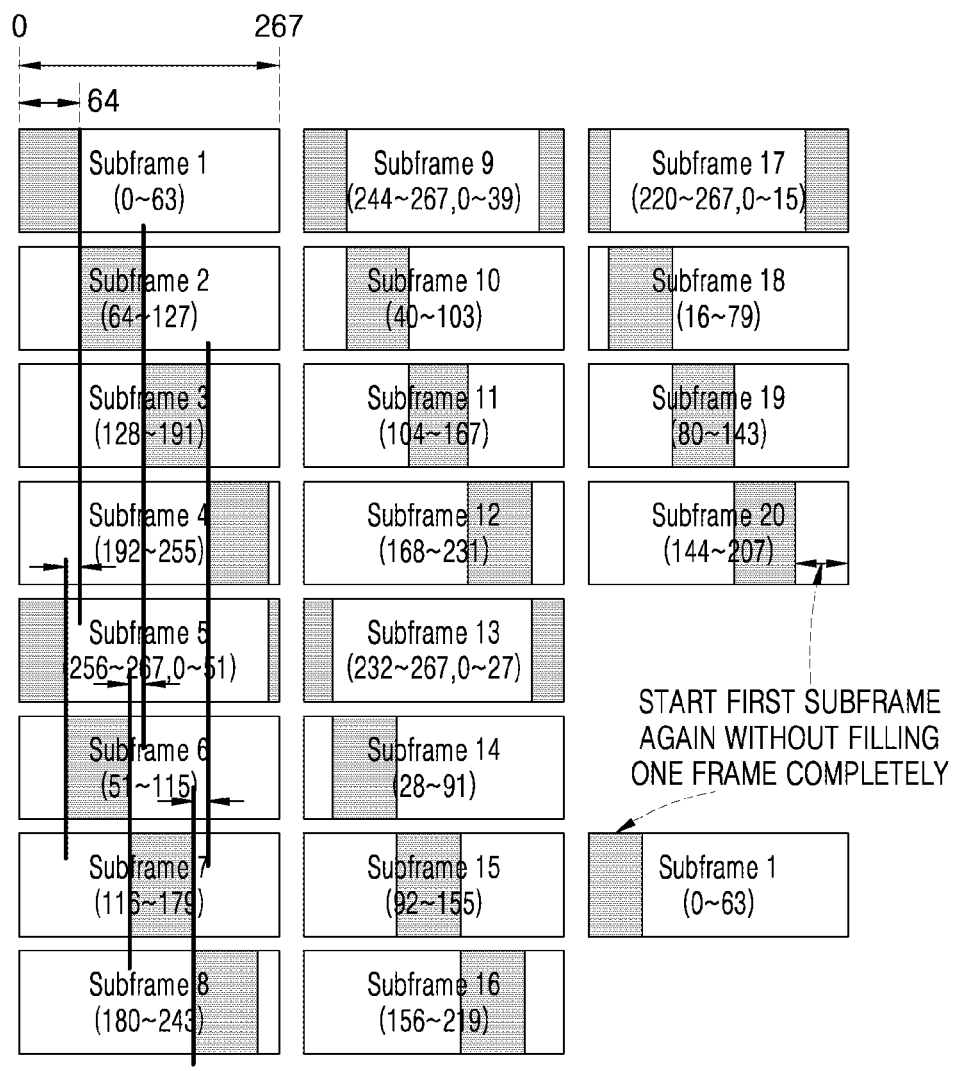
FIG. 7 illustrates a subframe sequence according to an embodiment.

FIG. 7 illustrates a subframe sequence according to an embodiment.

Referring to FIG. 7, an ultrasound imaging apparatus may select scan line groups by iteratively referring to a subframe sequence including 20 subframes. In an embodiment, the number of scan lines corresponding to each subframe is equally 64, and the subframe sequence may include 5 frames.

Referring to FIG. 7, the ultrasound imaging apparatus may generate a first frame including first through fourth subframes. Furthermore, the ultrasound imaging apparatus may generate a second frame including fifth through eighth subframes.

In an embodiment, a first scan line in each subframe may be set to be located next to a last scan line in its preceding subframe. Furthermore, the ultrasound imaging apparatus may set a scan line group such that a first scan line 0 is selected again after a last scan line 267 is selected. For example, the ultrasound imaging apparatus may set a scan line group including scan lines 256 through 267 and 0 through 51 corresponding to a fifth subframe after setting a scan line group including scan lines 192 through 255 corresponding to a fourth subframe.

According to an embodiment, the ultrasound imaging apparatus may set the number of scan lines corresponding to each subframe to a number other than a divisor of the number of all scan lines. In other words, the ultrasound imaging apparatus may set positions of subframes in consecutive frames to be different from each other by making a total number of scan lines in one frame different from the number of all the scan lines.

Furthermore, according to an embodiment, the ultrasound imaging apparatus may be configured to set the subframe sequence such that a last scan line 207 in a scan line group corresponding to a 20-th subframe that is a last subframe in the subframe sequence does not coincide with the last scan line 267 among all the scan lines. This configuration may efficiently reduce the number of subframes included in a sequence.

Figure 8:
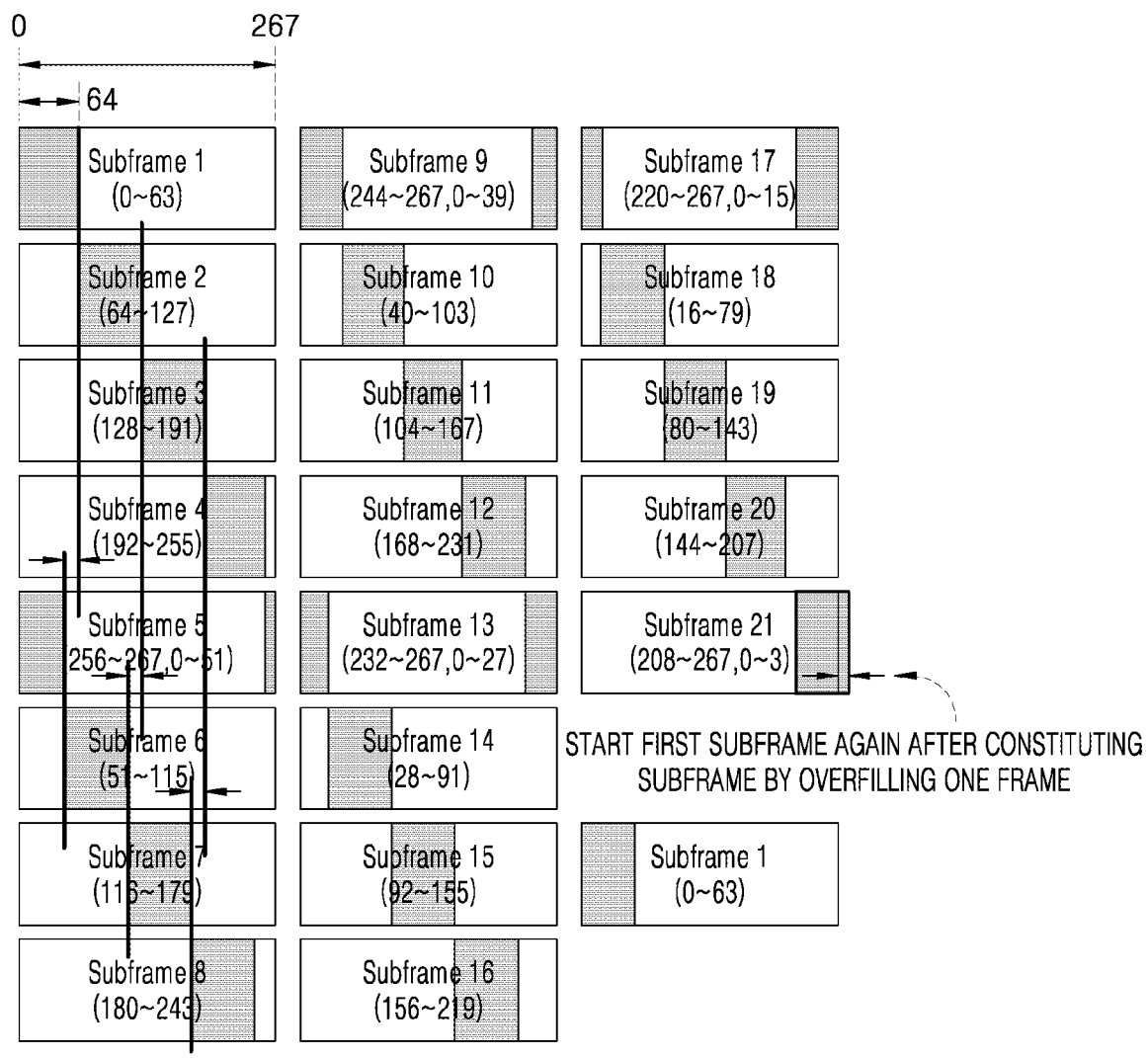
FIG. 8 illustrates a subframe sequence according to an embodiment.

FIG. 8 illustrates a subframe sequence according to an embodiment.

Referring to FIG. 8, the ultrasound imaging apparatus may select scan line groups by iteratively referring to a subframe sequence including 21 subframes. In an embodiment, the number of scan lines corresponding to each subframe is equally 64, and the subframe sequence may include 6 frames.

Referring to FIG. 8, the ultrasound imaging apparatus may generate a first frame including first through fourth subframes. Furthermore, the ultrasound imaging apparatus may generate a second frame including fifth through eighth subframes.

In an embodiment, a first scan line in each subframe may be set to be located next to a last scan line in its preceding subframe. Furthermore, the ultrasound imaging apparatus may set a scan line group such that a first scan line 0 is selected again after a last scan line 267 is selected. For example, the ultrasound imaging apparatus may set a scan line group including scan lines 256 through 267 and 0 through 51 corresponding to a fifth subframe after setting a scan line group including scan lines 192 through 255 corresponding to a fourth subframe.

According to an embodiment, the ultrasound imaging apparatus may set the number of scan lines corresponding to each subframe to a number that is not a divisor of the number of all scan lines. In other words, the ultrasound imaging apparatus may set positions of subframes in consecutive frames to be different from each other by making the number of scan lines in one frame different from the number of all the scan lines.

Furthermore, according to an embodiment, the ultrasound imaging apparatus may set the number of subframes included in one frame differently from the number of subframes in each of the other frames. For example, the ultrasound imaging apparatus may set a subframe in a sixth frame to be only a 21st subframe. This configuration may efficiently reduce the number of subframes included in a sequence.

Figure 9:
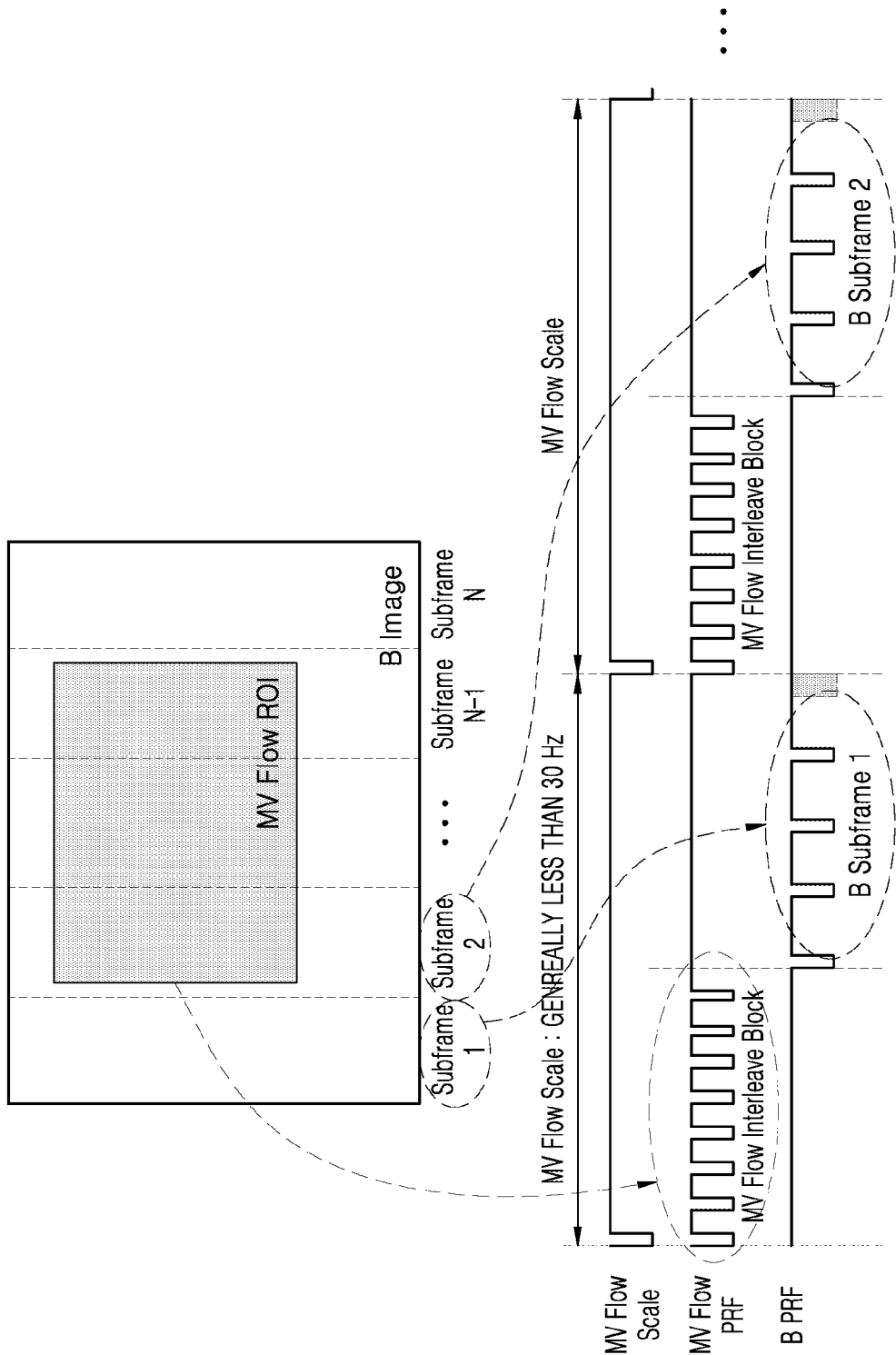
FIG. 9 illustrates a method of displaying a frame according to an embodiment.

FIG. 9 illustrates a method of displaying a frame according to an embodiment. More particularly, FIG. 9 illustrates a method of displaying one frame composed of a plurality of subframes when the plurality of subframes are acquired in an interleaved manner.

To simultaneously obtain different types of ultrasound images having different frame rates, an ultrasound imaging apparatus may use an interleaving method that involves dividing one frame into a plurality of subframes for acquisition. FIG. 9 illustrates an example in which the ultrasound imaging apparatus simultaneously obtains a B mode image showing intensity of an echo signal as brightness and a MV flow image showing blood flow. Furthermore, in the example, the ultrasound imaging apparatus obtains the B mode image on a subframe-by-subframe basis. However, this is merely an example, and it will be readily apparent to those of ordinary skill in the art that types of ultrasound images are not limited to the above-described types.

The ultrasound imaging apparatus may display the obtained B mode image and MV flow image together on a display. According to an embodiment, the ultrasound imaging apparatus may display the MV flow image and the B mode image in such a manner that they are superimposed on each other. However, the method of displaying an ultrasound image is not limited thereto.

Referring to FIG. 9, the ultrasound imaging apparatus may acquire a first frame of a MV flow image based on a MV flow interleave block pulse. In an embodiment, the MV flow interleave block pulse may be a group of pulses that are applied to acquire one frame of a MV flow image. In this case, before acquiring a subsequent frame of the MV flow image, the ultrasound imaging apparatus may obtain a first subframe image in a B mode image based on a B mode first subframe pulse B subframe 1. Furthermore, after acquiring a second frame of MV flow image based on a subsequent MV flow interleave block pulse, the ultrasound imaging apparatus may obtain a second subframe image in the B mode image based on a B mode second subframe pulse B subframe 2.

As shown in FIG. 9, the ultrasound imaging apparatus may use an interleaving method whereby one frame is divided into a plurality of subframes for acquisition to simultaneously obtain different types of ultrasound images having different frame rates. For example, the ultrasound imaging apparatus may alternately acquire in an interleaved manner ultrasound data for acquiring one frame of MV flow image and ultrasound data for acquiring a subframe in a B mode image. In this case, the ultrasound imaging apparatus may display an ultrasound image obtained on a subframe-by-subframe basis such that positions of subframes in consecutive frames may be different from each other as in the embodiments described with reference to FIGS. 3 through 8.

Figure 10:
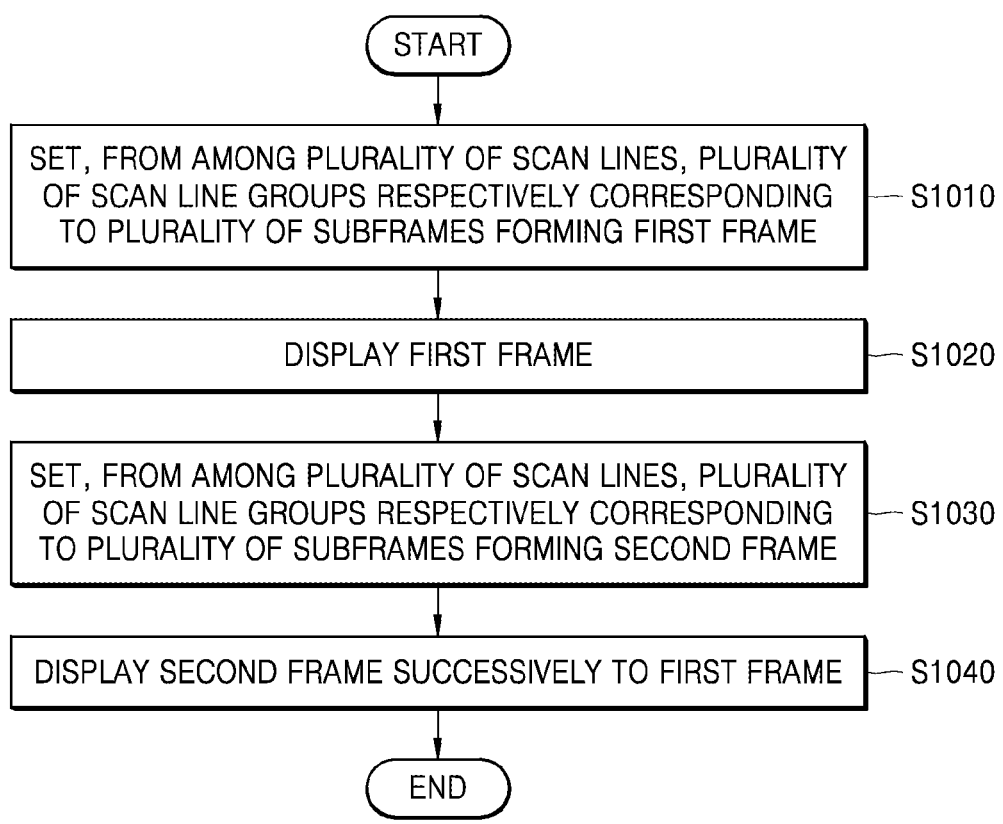
FIG. 10 is a flowchart of a method of displaying an ultrasound image, according to an embodiment.

FIG. 10 is a flowchart of a method of displaying an ultrasound image, according to an embodiment.

A plurality of scan line groups respectively corresponding to a plurality of subframes forming a first frame may be set from among a plurality of scan lines used for acquiring an ultrasound image of an ROI (S1010).

Each of the set scan line groups may include a plurality of scan lines for acquiring data corresponding to each subframe. According to an embodiment, the plurality of subframes may each have the same size. In other words, each scan line group corresponding to a subframe may include the same number of scan lines. In an embodiment, the plurality of subframes may be acquired in an interleaved manner. For example, a processor may discontinuously generate the plurality of subframes by allowing ultrasound signals to be discontinuously transmitted to the plurality of scan line groups.

The first frame is displayed on a display (S1020). The first frame may be displayed on a subframe-by-subframe basis. For example, the plurality of subframes constituting the first frame may be sequentially accumulated in the order that they are generated and then displayed. In detail, when the first frame includes first through third subframes, the first subframe may be displayed first, the first and second subframes may then be displayed together when the second subframe is generated, and finally the first through third subframes may be displayed together when the third subframe is generated. Alternatively, in an embodiment, the plurality of subframes forming the first frame may be displayed simultaneously.

A plurality of scan line groups respectively corresponding to a plurality of subframes forming a second frame may be set from among the plurality of scan lines (S1030). In this case, the second frame may be displayed successively to the first frame. Positions of the plurality of subframes forming the second frame may be different from positions of the plurality of subframes forming the first frame. In detail, the plurality of subframes forming the second frame may be set such that a position of a boundary line between adjacent ones of the subframes in the first frame does not overlap a position of a boundary line between adjacent ones of the subframes in the second frame.

The second frame may be displayed successively to the first frame (S1040). According to the method of displaying an ultrasound image, boundary lines between subframes respectively in frames displayed successively on the display do not overlap each other, and thus seam artifacts occurring in an ultrasound image may be reduced.

Embodiments may be implemented through non-transitory computer-readable recording media having recorded thereon computer-executable instructions and data. The instructions may be stored in the form of program codes, and when executed by a processor, may generate a predetermined program module to perform a specific operation. Furthermore, when being executed by the processor, the instructions may perform specific operations according to the embodiments.

What is claimed is:

1. An ultrasound imaging apparatus comprising:
  a display; and
  a processor configured to set, from among a plurality of scan lines, a plurality of scan line groups respectively corresponding to a plurality of subframes constituting a first frame, control the display to display the first frame, set, from among the plurality of scan lines, a plurality of scan line groups respectively corresponding to a plurality of subframes constituting a second frame, and control the display to display the second frame subsequently to the first frame,
  wherein the processor is further configured to set the plurality of scan line groups such that a position of a boundary line between adjacent ones of the plurality of subframes in the first frame does not overlap a position of a boundary line between adjacent ones of the plurality of subframes in the second frame,
  wherein the processor is further configured to set the plurality of scan line groups such that a foremost scan line corresponding to a foremost subframe among the plurality of subframes in the first frame is different from a foremost scan line corresponding to a foremost subframe among the plurality of subframes in the second frame.

2. The ultrasound imaging apparatus of claim 1, wherein each of the plurality of scan line groups comprises the same number of scan lines.

3. The ultrasound imaging apparatus of claim 2, wherein the processor is further configured to set the number of scan lines included in each of the plurality of scan line groups to a number that is not a divisor of the number of the plurality of scan lines.

4. The ultrasound imaging apparatus of claim 1, wherein the processor is further configured to set the plurality of scan line groups such that the foremost scan line corresponding to the foremost subframe among the plurality of subframes in the second frame is located next to a backmost scan line corresponding to a backmost subframe among the plurality of subframes in the first frame.

5. The ultrasound imaging apparatus of claim 1, wherein the processor is further configured to acquire the plurality of subframes respectively constituting the first and second frames in an interleaved manner.

6. The ultrasound imaging apparatus of claim 5, wherein the plurality of subframes are acquired based on a first type of ultrasound imaging method, and
wherein the processor is further configured to:
obtain a second ultrasound image on a full frame basis based on a second type of ultrasound imaging method; and
control the display to simultaneously display the first frame and the second ultrasound image.

7. The ultrasound imaging apparatus of claim 1, wherein the processor is further configured to generate the first frame by arranging the plurality of subframes in the first frame adjacent to one another.

8. The ultrasound imaging apparatus of claim 7, wherein the processor is further configured to control the display such that the plurality of subframes constituting the first frame are sequentially accumulated and displayed.

9. The ultrasound imaging apparatus of claim 7, wherein the processor is further configured to control the display to simultaneously display the plurality of subframes constituting the first frame.

10. The ultrasound imaging apparatus of claim 9, further comprising a memory storing a predetermined sequence,
wherein the processor is further configured to set the plurality of scan line groups based on the predetermined sequence stored in the memory.

11. A method of displaying an ultrasound image, the method comprising:
setting, from among a plurality of scan lines, a plurality of scan line groups respectively corresponding to a plurality of subframes constituting a first frame and displaying the first frame; and
setting, from among the plurality of scan lines, a plurality of scan line groups respectively corresponding to a plurality of subframes constituting a second frame and displaying the second frame subsequently to the first frame,
wherein the plurality of scan line groups are set such that a position of a boundary line between adjacent ones of the plurality of subframes in the first frame does not overlap a position of a boundary line between adjacent ones of the plurality of subframes in the second frame,
wherein the plurality of scan line groups are set such that a foremost scan line corresponding to a foremost subframe among the plurality of subframes in the first frame is different from a foremost scan line corresponding to a foremost subframe among the plurality of subframes in the second frame.

12. The method of claim 11, wherein each of the plurality of scan line groups comprises the same number of scan lines.

13. The method of claim 12, wherein the number of scan lines included in each of the plurality of scan line groups is set to a number that is not a divisor of the number of the plurality of scan lines.

14. The method of claim 11, wherein the plurality of scan line groups are set such that the foremost scan line corresponding to the foremost subframe among the plurality of subframes in the second frame is located next to backmost scan line corresponding to backmost subframe among the plurality of subframes in the first frame.

15. The method of claim 11, wherein the plurality of subframes respectively constituting the first and second frames are acquired in an interleaved manner.

16. The method of claim 12, wherein the plurality of subframes are acquired based on a first type of ultrasound imaging method, the method further comprising:
obtaining a second ultrasound image on a full frame basis based on a second type of ultrasound imaging method,
wherein the displaying of the first frame comprises displaying the first frame and the second ultrasound image simultaneously.

17. The method of claim 11, wherein the first frame is generated by arranging the plurality of subframes in the first frame adjacent to one another.

18. The method of claim 17, wherein the displaying of the first frame comprises sequentially accumulating the plurality of subframes constituting the first frame and displaying a result of the sequentially accumulating.

19. The method of claim 17, wherein the displaying of the first frame comprises simultaneously displaying the plurality of subframes constituting the first frame.

20. A non-transitory computer-readable recording medium having stored therein a computer program code which, when read and executed by a processor, performs a method of displaying an ultrasound image, the method comprising:
setting, from among a plurality of scan lines, a plurality of scan line groups respectively corresponding to a plurality of subframes constituting a first frame and displaying the first frame; and
setting, from among the plurality of scan lines, a plurality of scan line groups respectively corresponding to a plurality of subframes constituting a second frame and displaying the second frame subsequently to the first frame,
wherein the plurality of scan line groups are set such that a position of a boundary line between adjacent ones of the plurality of subframes in the first frame does not overlap a position of a boundary line between adjacent ones of the plurality of subframes in the second frame,
wherein the plurality of scan line groups are set such that a foremost scan line corresponding to a foremost subframe among the plurality of subframes in the first frame is different from a foremost scan line corresponding to a foremost subframe among the plurality of subframes in the second frame.

* * * * *